United States Patent
Choudary et al.

(10) Patent No.: US 6,274,741 B1
(45) Date of Patent: Aug. 14, 2001

(54) PROCESS FOR THE PREPARATION OF ACYL HETEROAROMATIC COMPOUNDS FROM HETEROAROMATIC COMPOUNDS BY METAL ION EXCHANGED CLAYS

(75) Inventors: Boyapati Manoranjan Choudary; Mutyala Sateesh; Mannepalli Lakshmi Kantam; Kondapuram Vijaya Raghaven, all of Hyberabad (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 09/538,095

(22) Filed: Mar. 29, 2000

(51) Int. Cl.[7] .................. C07D 207/333; C07D 307/40; C07D 307/50; C07D 333/22
(52) U.S. Cl. ................ 548/540; 549/70; 549/483; 549/489
(58) Field of Search ................ 548/540; 549/70, 549/783

(56) References Cited

PUBLICATIONS

Jackson et al., "Reactions on Solid Supports Part II: A Convenient Method for Synthesis of Pyrromethanes Using a Montmorillonite Clay As Catalyst," Tetrahedron Letters, vol. 26, No. 6, pp. 793–796, 1985.*

* cited by examiner

*Primary Examiner*—Jane C. Oswecki
(74) *Attorney, Agent, or Firm*—Samuels, Gauthier & Stevens

(57) ABSTRACT

The present invention relates to a process for the preparation of the acyl heteroaromatic compounds useful as important intermediates for drugs, pharmaceuticals and flavouring agents, said process comprising reacting an heteroaromatic compound selected from furan, thiophene and pyrrole with a C2–C5 acid anhydride as an acylating agent employing metal ion exchanged clays as catalysts at temperatures in the range of 0–130° C. for a period of 1–24 h, and separating the acyl heteroaromatic compound by a conventional method to obtain a product of high purity.

11 Claims, No Drawings

PROCESS FOR THE PREPARATION OF ACYL HETEROAROMATIC COMPOUNDS FROM HETEROAROMATIC COMPOUNDS BY METAL ION EXCHANGED CLAYS

FIELD OF THE INVENTION

The present invention relates to an improved process for the preparation of acyl heteroaromatic compounds from heteroaromatic compounds, important intermediates for drugs, pharmaceuticals and flavoring agents for foodstuffs. More particularly, this invention relates a process for the preparation of acyl heteroaromatic compounds of high purity from heteroaromatic compounds using C2–C5 acid anhydrides as acylating agents in the presence of metal exchanged clays.

BACKGROUND OF THE INVENTION

This invention particularly relates to an ecofriendly process for the preparation of acyl heteroaromatic compounds from heteroaromatic compounds using acid anhydrides as acylating agents and metal exchanged clays as catalysts dispensing the use of stoichiometric amounts of corrosive, toxic aluminium chloride and other Lewis and protic acids as Friedel-Crafts reagents. The acylated products are valuable intermediates for drugs, pharmaceuticals, flavours and fragrances.

2-acetylthiophene is normally prepared by Friedel-Crafts acetylation of thiophene with acetic acid, acetyl chloride or acetic anhydride in the presence of a Lewis acid or a proton acid. The product is purified by distillation and it regularly contains from 1–2% of 3-acetyl thiophene as an impurity. For most purposes 2-acetylthiophene of 98–99% is adequate.

PRIOR ART REFERENCES

Reference may be made to publication by Finan et al, Journal Chemical Society, 2728, 1963 Wherein 2-acylfuran derivatives are prepared from furans using $BF_3.Et_2O$. The Drawbacks are $BF_3.Et_2O$ is expensive and difficult to handle.

Reference may be made to a U.S. Pat. No. 4,266,066 wherein acylated compounds are prepared by reacting carboxylic acid halides, in particular carboxylic acid chlorides, with aluminium-alkyl compounds at a temperature between 20–100° C. The reaction mixture is worked up in usual manner, suitably by decomposition with water followed by distillation. The draw-backs in the above processes are the use of stoichiometric amounts of aluminium compounds, an hazardous material that leaves large amount of solid wastes after the reaction and tedious separation process from the alumina get to obtain the product.

Reference may be made to a German patent, Ger. Offen. DE3,618,964 and to a publication by Hoelderich et al., Studies in Surface Science and Catalysts, 49A,69, 1989, wherein a procedure for vapour phase acylation of heteroaromatics with acylating agents in the presence of zeolite catalysts is describes. The main drawbacks are the yields of the acyl heteroaromatics are poor, 23–41% and the vapor phase reaction requires more energies.

Reference may be made to Kirk-Othmer, Encyclopedia of Chemical Technology, Vol 24, IVth edition, p38,1997, wherein acylation of thiophene is carried out with acid anhydrides in presence of phosphoric acid or other catalysts like $AlCl_2$, $SnCl_4ZnCl_2$ with acid chlorides. The draw back is all the reactions give between 0.5% and 2.0% of 3-isomer.

There has been much striving to find catalyst systems that minimize the 3-isomer content attempting to meet the customers specification.

Reference may be made to a U.S. Pat. No. 5,371,240 wherein 3-acetylthiophene contaminating 2-acetylthiophene, is removed by a selective electrophilic substitution process, bromination, followed by fractional distillation. The drawback is an additional step, bromination is required to get the pure product.

Reference may be made to a publication by Fripiat et al., Journal Catalysis, 182, 257, 1999 wherein the acylation of thiophene with butyryl chloride is been carried out in the presence of zeolites in quantitative yields in liquid phase. The draw back is synthetic zeolites are expensive.

The inherent disadvantages in the use of conventional Lewis acid metal chlorides for Friedel-Crafts acylation are that they are non-regenerable and require more than stoichiometric amounts because of complexation with the carbonyl product formed. Work-up to decompose the resultant intermediate complex by hydrolysis forms a large amount of waste product and separation is lengthy and expensive.

Obviously, different approaches have been employed for the preparation of acyl heteroaromatic compounds. There was therefore a need for a process for the preparation of acyl heteroaromatic compounds which is simple to operate and can be carried out in a media which are not toxic and/or corrosive. Moreover the catalyst should be simple to separate and reusable.

OBJECTS OF THE INVENTION

The main object of the present invention is to provide an improved process for the preparation of acylheteroaromatic compounds from heteroaromatic compounds selected from thiophene, furan and pyrrole using C2–C5 acid anhydrides as acylating agents in the presence of metal ion exchanged clays at a temperature in the range of 0 to 130° C. for 1–24 h and separating the acyl heteroaromatic compound by a conventional method to obtain a product of high purity, which obviates the drawbacks as detailed above.

Another object of the present invention is the use of the metal ion exchanged clays as catalysts, sourced from cheaper and natural clays.

Another object of the present invention is metal ions selected for exchange are $Fe^{3+}, Zn^{2+}, Cu^{2+}, Al^{3+}La^{3+}$ Another object of the present invention is heteroaromtic compounds selected are thiophene, furan and pyrrole.

Still another object of the present invention is quantity of catalyst used is 1 to 30% by weight with respect to the acylating agent.

Still another object of the present invention is the use of C2–C5 acid anhydrides as acylating agents.

Still another object of the present invention is the ratio of heteroaromatic compound and acylating agent is 5:1 to 1:5.

Yet another object of the present invention is the reaction is effected at a temperature in the range of 0 to 130° C. for 1–24 h.

SUMMARY OF THE INVENTION

The novelty of the present invention lies in the use of metal ion exchanged clays obtained easily by ion exchange process from naturally available montmorillonite and acid treated montmorillonite for the acylation of heteroaromatic compounds such as furan, thiophene, and pyrrole to afford 2-acyl heteroaromatic compounds selectively >99% in excellent yields for the first time. The 2-acyl heteroaromatic compounds thus obtained are devoid of the regioisomer, 3-acyl heteroaromatic compound usual contaminant in the acylation process employing soluble Lewis acids. Thus this invention offers highly pure and desired isomer to be used as an intermediate for specialised drugs and pharmaceuticals. Unlike soluble Lewis acids, the solid catalysts employed here does not produce any effluents. Since the catalyst is cheap and reusable for several times under mild reaction conditions, the process invented here is not only ecofriendly but also economically viable.

DETAILED DESCRIPTION OF THE INVENTION

Accordingly, the present invention provides an improved process for the preparation of acyl heteroaromatic compounds, important intermediates for drugs, pharmaceuticals and flavouring agents wherein the said process comprises reacting an heteroaromatic compound selected from furan, thiophene and pyrrole with a C2–C5 acid anhydride as an acylating agent employing metal ion exchanged clays as catalysts at temperatures in the range of 0–130° C. for a period of 1–24 h, and separating the acyl heteroaromatic compound by a conventional method to obtain a product of high purity.

In an embodiment of the invention, the catalysts used are metal ion exchanged clays.

In an embodiment of the invention, the catalysts used are the metal ion exchanged clays which are obtained easily from natural montmorillonites or acid treated montmorillonites.

In an embodiment of the invention metal exchanged clays used are $Fe^{3+}$, $Zn^{2+}$, $Cu^{2+}$, $Al^{3+}La^{3+}$ exchanged clays.

In an embodiment of the invention the metal ion exchanged clays are prepared from cheaper and naturally available clays.

In an embodiment of the invention metal ions used for exchange are $Fe^{3+}$, $Zn^{2+}$, $Cu^{2+}$, $Al^{3+}La^{3+}$.

In an embodiment of the invention, acylating agents used are selected from C2–C5 acid anhydrides, acetic anhydride to valeric anhydride.

In another embodiment of the present invention, the reaction is, preferably, effected at a temperature in the range of 20 to 80° C. for 2–12 hrs.

In yet another embodiment of the present invention, the affords 2-acyl heteroaromatic compound selectively >99% in excellent yield.

In still another embodiment of the present invention, the 2-acyl heteraromatic compound obtained can be directly used without further purification to obtain specialised drugs and pharmaceuticals.

One more embodiment of the present invention, the ratio of the heteroaromatic compound and acylating agent is 5:1 and the solvents selected for reaction are heteroaromatics and self solvents.

SCIENTIFIC EXPLANATION

The use of metal ion exchanged clays obtained easily by cation exchanged process from naturally available montmorillonite and acid treated montmorillonite for the acylation of heteroaromatic compounds such as furan, thiophene, and pyrrole afforded 2-acyl heteroaromatics selectively >99% in excellent yields. Lewis acidity predominantly present in clays generates acyl cation electrophile effectively from acid anhydride, a prerequisite for Friedel-Crafts electrophilic substitution. The formation of 2-acyl heteroaromatic compound selectively is due to electronic effects favoured by strong Lewis acidity of the clay catalysts used here that generates facile electrophile. Unlike soluble Lewis acids, the solid catalysts employed here does not produce any effluents. Since the catalyst is cheap, reusable for several times under mild reaction conditions, the process invented here is not only ecofriendly but also economically viable.

Metal ion exchanged clays are prepared as in example 1 and employed them in the acylation of heteroaromatic compounds with acid anhydrides as described in the examples.

The following examples are given by way of illustration of the present invention and therefore should not be construed to limit the scope of the invention.

EXAMPLE 1

Catalyst Preparation a) K10 montmorillonite—Montmorillonite employed in the synthesis was obtained from (Fluka Grade K10) with exchange capacity of 8.0 equiv.

b) $Fe^{3+}$-exchanged montmorillonite catalyst: To a 1 lt. stirred aqueous solution of $FeCl_3$ (1.0M), 80 g of K10-montmorillonite was added. Stirring maintained for 16–30 hrs in order to saturate the exchange capacity of montmorillonite K10. The clay suspension was centrifuged and the supernatant solution was discharged. The clay catalyst was filtered, and washed with distilled water and the washing cycles were repeated until disappearance of $Cl^-$ ions from the discarded water. The clay was dried overnight in an oven at 120° C. and finely ground in a mortar.

c) $Zn^{2+}$-exchanged catalyst: It was prepared in the same manner as in example b, stirring 1M solution of $ZnCl_2$ and 80 g of K10 montmorillonite.

EXAMPLE 2

A mixture of pyrrole (40 mmoles) acetic anhydride (10 mmoles) and $Fe^{3+}$-exchanged clay catalyst (0.5 g) were stirred in a round bottomed flask (50 ml) under nitrogen atmosphere at room temperature. After completion of the reaction (followed by G.C. ), the mixture was filtered and distilled the reaction mixture to obtain the crude product. Yield: 0.9 g

EXAMPLE 3

A mixture of pyrrole (40 mmoles) acetic anhydride (10 mmole) and $Fe^{3+}$-exchanged clay catalyst (0.5 g) were stirred in a round bottomed flask (50 ml) under nitrogen atmosphere at 80° C. temperature. After completion of the reaction (followed by G.C.), the reaction mixture was filtered and distilled the reaction mixture to obtain the crude product. Yield: 1.0 g

EXAMPLE 4

A mixture of pyrrole (40 mmoles) acetic anhydride (10 mmoles) and K10 montmorillonite catalyst (0.5 g) were stirred in a round bottomed flask (50 ml) under nitrogen atmosphere at 80° C. temperature. After completion of the reaction (followed by G.C.), the reaction mixture was filtered and distilled the reaction mixture to obtain the crude product. Yield: 0.6 g

EXAMPLE 5

A mixture of pyrrole (40 mmoles) acetic anhydride (10 mmoles) and $Zn^{2+}$-exchanged clay catalyst (0.5 g) were stirred in a round bottomed flask (50 ml) under nitrogen atmosphere at 80° C. temperature. After completion of the reaction (followed by G.C.), the reaction mixture was filtered and distilled the reaction mixture to obtain the crude product. Yield: 0.9 g

EXAMPLE 6

A mixture of thiophene (50 mmol), acetic anhydride (10 mmol) and $Fe^{3+}$-exchanged clay catalyst (0.5 g) were stirred in a round bottomed flask (50 ml) under nitrogen atmosphere at room temperature. After completion of the reaction (followed by G.C.), the reaction mixture was filtered and distilled the reaction mixture to obtain the crude product. Yield: 0.7 g

EXAMPLE 7

A mixture of thiophene (50 mmol), acetic anhydride (10 mmol) and $Fe^{3+}$-exchanged clay catalyst (0.5 g) were stirred in a round bottomed flask (50 ml) under nitrogen atmosphere at 80° C. temperature. After completion of the reaction (followed by G.C.), the reaction mixture was filtered and distilled the reaction mixture to obtain the crude product. Yield: 1.2 g

EXAMPLE 8

A mixture of thiophene (50 mmol), acetic anhydride (10 mmol) and $Zn^{2+}$-exchanged clay catalyst (0.5 g) were stirred in a round bottomed flask (50 ml) under nitrogen atmosphere at 80° C. temperature. After completion of the reaction (followed by G.C.), the reaction mixture was filtered and distilled the reaction mixture to obtain the crude product. Yield: 1.1 g

EXAMPLE 9

A mixture of furan (50 mmol), acetic anhydride (10 mmol) and $Fe^{3+}$-exchanged clay catalyst (0.5 g) were stirred in a round bottomed flask (50 ml) under nitrogen atmosphere at room temperature. After completion of the reaction (followed by G.C.), the reaction mixture was filtered and distilled the reaction mixture to obtain the crude product. Yield: 1.0 g

EXAMPLE 10

A mixture of furan (50 mmol), acetic anhydride (10 mmol) and $Fe^{3+}$-exchanged clay catalyst (0.5 g) were stirred in a round bottomed flask (50 ml) under nitrogen atmosphere at room temperature. After completion of the reaction (followed by G.C.), the reaction mixture was filtered and distilled the reaction mixture to obtain the crude product. Yield: 0.9 g

EXAMPLE 11

A mixture of furan (50 mmol), acetic anhydride (10 mmol) and $Zn^{2+}$-exchanged clay catalyst (0.5 g) were stirred in a round bottomed flask (50 ml) under nitrogen atmosphere at room temperature. After completion of the reaction (followed by G.C.), the reaction mixture was filtered and distilled the reaction mixture to obtain the crude product. Yield: 0.8 g

TABLE 1

Acetylation of heteroaromatic compounds with acetic anhydride in the presence of metal ion exchanged clays

| Example No. | Heteroaromatic compound | Catalyst | Temp (° C.) | Time (h) | Isolated Yields(%)[a] | Product distribution | |
|---|---|---|---|---|---|---|---|
| | | | | | | 2-Acetyl heteroatom | others |
| 2 | Pyrrole | $Fe^{3+}$-mont. | RT | 12 | 86 | >99% | — |
| 3 | Pyrrole | $Fe^{3+}$-mont. | 80 | 6 | 98 | 95 | 5 |
| 4 | Pyrrole | K10-mont. | 80 | 8 | 60 | 96 | 4 |
| 5 | pyrrole | $Zn^{2+}$-mont. | 80 | 6 | 87 | 95 | 5 |
| 6 | Thiophene | $Fe^{3+}$-mont | RT | 8 | 56 | >99% | — |
| 7 | Thiophene | $Fe^{3+}$-mont. | 80 | 5 | 97 | >99% | — |
| 8 | Thiophene | $Zn^{2+}$-mont. | 80 | 5 | 92 | >99% | — |
| 9 | Furan | $Fe^{3+}$-mont. | 40 | 8 | 98 | 92 | 8 |
| 10 | Furan | $Fe^{3+}$-mont. | RT | 12 | 82 | >99% | — |
| 11 | Furan | $Zn^{2+}$-mont. | RT | 12 | 77 | >99% | — |

[a]based on acetic anhydride

The present process has several advantages as described below:

1. A novel and ecofriendly process for the manufacture of acyl heteroaromatic compounds.
2. The present process eliminates the use of corrosive and stoichiometric quantities aluminium chloride and other Lewis and protic acid catalysts.
3. Metal ion exchanged have been used as catalysts for the acylation of heteroaromatic compounds in excellent yields for the first time.
4. The selectively towards 2-acyl heteroaromatic compounds is greater than 99% in the presence of clays as catalysts.
5. The product is devoid of 3-acyl heteroaromatic compound, usually formed in the acylation process using soluble Lewis acids.
6. The 2-acyl heteroaromatic compounds thus obtained can be directly used for the preparation of specialised drugs and pharmaceuticals.
7. Work-up procedure is simple.
8. The present process envisages no disposal problem as the catalyst can be used for several cycles. The catalyst was subjected to several recycles which displayed consistent activity.
9. The present process is environmentally safe since there is no disposal problem.
10. The process is economical.

What is claimed is:

1. A process for the preparation of acyl heteroaromatic compound useful as, important intermediates for drugs, pharmaceuticals and flavoring agents, said process comprising reacting a heteroaromatic compound selected from furan, thiophene and pyrrole with a C2–C5 acid anhydride as an acylating agent employing metal ion exchanged clays as catalysts at temperatures in the range of 0–130° C. for a period of 1–24 h, and separating the acyl heteroaromatic compound by a conventional method to obtain a product of high purity.

2. A process as claimed in claim 1 wherein the catalysts used are metal ion-exchanged clays.

3. A process as claimed in claim 1 wherein the metal exchanged clays are selected from $Fe^{3+}$, $Zn^{2+}$, $Cu^{2+}$, $Al^{3+}$ $La^{3+}$-exchanged clays.

4. A process as claimed in claim 1 wherein the metal ion exchanged clays are prepared from naturally available clays which render them inexpensive.

5. A process as claimed in claim 1 wherein the catalyst used are the metal ion exchanged clays obtained by cation exchange of natural montmorillonites or acid treated montmorillonites.

6. A process as claimed in claim 1 wherein C2–C5 acid anhydrides used are selected from acetic anhydride to valeric anhydride as acylating agents.

7. A process as claimed in claim 1 wherein, the reactions is effected at a temperature in the range of 20to 80° C. for 2–12 hrs.

8. A process as claimed in claim 1 wherein the ratio of heteroaromatic compound and acylating agent is 5:1.

9. A process as claimed in claim 1 wherein solvents selected for the reaction are heteroaromatic as self solvents.

10. A process as claimed in claim 1 wherein the reaction affords 2-acyl heteroaromatic compound selectively >99%.

11. A process as claimed in claim 1 wherein the 2-acyl heteroaromatic compound obtained can be directly used without further purification to obtain drugs and pharmaceuticals.

* * * * *